United States Patent
Allred

(10) Patent No.: US 6,814,794 B2
(45) Date of Patent: Nov. 9, 2004

(54) TEMPORARY DENTAL CEMENTS HAVING REDUCED TOOTH SENSITIVITY

(75) Inventor: Peter M. Allred, Riverton, UT (US)

(73) Assignee: Ultradent Products, Inc., South Jordan, UT (US)

( * ) Notice: Subject to any disclaimer, the term of this patent is extended or adjusted under 35 U.S.C. 154(b) by 0 days.

(21) Appl. No.: 10/288,775

(22) Filed: Nov. 6, 2002

(65) Prior Publication Data

US 2004/0086830 A1 May 6, 2004

(51) Int. Cl.$^7$ ................................................. A61K 6/08
(52) U.S. Cl. ...................... 106/35; 523/115; 523/116; 433/89; 433/90; 433/226; 433/228.1
(58) Field of Search .................. 106/35; 433/89, 433/90, 226, 228.1; 523/115, 116

(56) References Cited

U.S. PATENT DOCUMENTS

| | | | |
|---|---|---|---|
| 4,343,608 A * | 8/1982 | Hodosh | 433/224 |
| 4,773,933 A | 9/1988 | Futami et al. | 106/35 |
| 5,154,613 A * | 10/1992 | Cohen | 433/228.1 |
| 5,534,562 A | 7/1996 | Jensen et al. | 523/118 |
| 5,554,027 A | 9/1996 | Br.ang.nemark | 433/172 |
| 5,639,239 A | 6/1997 | Earle | 433/218 |
| 5,708,052 A | 1/1998 | Fischer et al. | 523/116 |
| 5,824,720 A | 10/1998 | Nowak et al. | 523/116 |
| 5,859,089 A | 1/1999 | Qian | 523/116 |
| 6,034,152 A | 3/2000 | Burger et al. | 523/116 |
| 6,127,451 A | 10/2000 | Qian | 523/116 |
| 6,133,339 A | 10/2000 | Xie et al. | 523/116 |
| 6,206,192 B1 * | 3/2001 | Winstead et al. | 206/572 |
| 6,306,206 B1 * | 10/2001 | Fischer et al. | 106/35 |
| 6,353,041 B1 | 3/2002 | Qian | 523/116 |
| 2002/0082317 A1 * | 6/2002 | Lyons et al. | 523/116 |

* cited by examiner

Primary Examiner—C. Melissa Koslow
(74) Attorney, Agent, or Firm—Workman Nydegger

(57) ABSTRACT

Temporary dental cements used to temporarily affix a dental prosthesis or appliance to a tooth or other dental substrate includes one or more soothing agent to prevent or reduce tooth sensitivity. The temporary dental cement includes a mixture of an ion leaching agent, polycarboxylic acid, a soothing agent and water. The soothing agent (e.g., 2-ethoxybenzoic acid and 2-methoxy-4-methylphenol) is added in an amount so as to reduce or eliminate tooth sensitivity associated with the reaction between the polycarboxylic and the ion leaching agent (base). The temporary cement composition is sufficiently hydrophilic that it can be readily removed from the tooth when it is desired to permanently restore the tooth.

43 Claims, No Drawings

TEMPORARY DENTAL CEMENTS HAVING REDUCED TOOTH SENSITIVITY

CROSS-REFERENCE TO RELATED APPLICATIONS

Not applicable.

BACKGROUND OF THE INVENTION

1. The Field of the Invention

The invention is in the field of dental bonding compositions, more particularly temporary dental cements used to temporarily bond a dental prosthesis to a person's tooth.

2. The Relevant Technology

Permanent dental cements are employed to adhere a dental appliance or prosthesis to a tooth which has been prepared to receive the prosthesis or appliance. Permanent dental cements typically comprise two parts, with one part comprising a glass ionomer silica and a second part comprising a polyacrylic acid. Mixing together the glass ionomer silica and aqueous polyacrylic acid results in an acid-base reaction that yields a salt. The salt has a matrix which forms a strong bond between the tooth and a prosthesis or appliance.

When resins are employed as a permanent bonding material, such as luting cements for crowns, the deposition of the final permanent bonding material is typically preceded by the application of a hydrophilic resin primer to the tooth preparation. Bonding primers bond to the tooth surface, after which the permanent resin-based luting cement is bonded onto the bonding primer. The use of a bonding primer increases the overall adhesion of the luting cement to the tooth.

Although permanent dental cements are highly useful for a variety of different dental purposes where a permanent bond is desired, it may be desirable in some cases to temporarily affix a prosthesis or appliance to a tooth, then later remove the prosthesis or appliance. For example, before mounting a permanent crown on a tooth which has been prepared to receive the crown, a dentist typically makes an impression of the tooth. The dentist then mounts a temporary crown on the tooth and sends the impression to a laboratory for manufacture of the permanent crown.

The temporary crown is held in place by a temporary dental cement until the permanent crown is prepared. Thereafter, the temporary crown is removed. The permanent crown is then permanently affixed to the tooth through the use of a permanent dental cement. One type of temporary dental cement comprises eugenol, rosin, pine gum, or tall oil mixed with zinc oxide. One problem with such dental cements is that they are hydrophobic. Because of this, such temporary cements are not able to form a chemical seal both with and against the tooth. Forming a poor seal can lead to tooth sensitivity and infection.

Another problem is that such temporary dental cements are hard to remove completely. They can leave an insoluble, oily residue on a tooth and/or contaminate the underlying dentin and/or enamel so as to inhibit or prevent the later formation of a permanent bond after removal of the temporary cement. This oily residue can be difficult to remove, particularly by rinsing with water or through the use of conventional drying agents used in the dental art. The oily residues do not bond well to hydrophilic primers and can even inhibit polymerization of hydrophobic resins. Thus, temporary cements that contain eugenol or other hydrophobic oils or resins must generally be cleaned off with another hydrophobic composition, such as oil of orange, or another hydrophobic cleaner. Furthermore, typical hydrophobic temporary cements, such as eugenol, can also be irritating to nerve and pulp tissues. For these and other reasons, temporary bonding cements comprising eugenol or other hydrophobic oils or resins have become highly disfavored by many dental practitioners.

In view of the foregoing problems inherent in eugenol-based or other hydrophobic temporary dental cements, some have proposed the use of more hydrophilic temporary dental cements. The theory behind using a hydrophilic temporary cement is that hydrophilic materials are more chemically compatible with dental tissues and, as such, would be expected to form a better bond and seal against a patient's tooth. In addition, temporary bonding cements that are hydrophilic would be expected to be more easily washed off using water or mixtures of water and hydrophilic solvents.

Nevertheless, whereas hydrophilic temporary bonding cements have solved some problems associated with hydrophobic temporary cements, they have created other problems. For example, U.S. Pat. No. 6,306,206 to Fischer et al., discloses a temporary dental cement that is similar to permanent dental cements in that it employs a two-part system involving an ion leaching agent and a polyacrylic acid, but that has been modified so as to include a sugar or sugar-derivative in order to form a more temporary bond that can be more easily removed at a later time. For purposes of disclosing temporary dental compositions and methods of preparing and using such compositions, the foregoing patent is incorporated by reference. One drawback of such compositions, or even permanent dental cements based on similar chemistry, is that they can cause significant pain to the patient when first applied. As a result, it is recommended that such compositions only be used on patients under anesthesia.

In view of the foregoing, there is a need to provide temporary dental cements that are able to form a good bond and seal against the tooth but which do not cause significant pain when applied to a patient's tooth. This is especially true in the case where a patient or other person needs to temporarily fix a tooth, such as a filling or crown that has become dislodged, or to temporarily repair a painful cavity or a tooth that has been broken at a time when it is inconvenient or impossible to visit a dentist.

Improved temporary dental cements and methods for temporarily repairing a person's tooth with reduced sensitivity are disclosed and claimed herein.

SUMMARY OF THE INVENTION

The present invention relates to temporary dental cements having reduced tooth sensitivity when placed against a person's tooth. The invention also relates to kits and methods that utilize such compositions. The inventive compositions can be used by dental practitioners when attaching a temporary prosthesis to a patient's tooth, as well as by persons who need to temporarily repair a broken or dislodged dental prosthesis or tooth defect outside the context of a visit to a dental practitioner.

Such temporary dental cements can be sold over-the-counter in order to allow a person to repair his or her own tooth without the immediate assistance of a dental practitioner. This may occur, for example, when a person is traveling or is in a remote location and cannot immediately visit a dentist. Or the person may have an emergency that arises at night, over the weekend or during some other time frame when it is inconvenient or impossible to visit a dentist. The inventive compositions may, of course, be used by a dental practitioner to temporarily bond a dental prosthesis to a patient's tooth with reduced pain or sensitivity.

The temporary dental cements according to the invention comprise an acid in one component and a base in another component which, when mixed together in the presence of water, react to form a curable material that is capable of bonding to a person's tooth. The acid component is typically a polycarboxylic acid (e.g., polyacrylic acid) that is hydrophilic. The base component is typically a metal oxide (e.g., zinc oxide) or other ion leaching agent that reacts with the acid component.

The two components are mixed together prior to application, which causes them to undergo an acid-based reaction so as to form a metal carboxylate polymer that is able to adhere to teeth. The metal carboxylate polymer can also serve as a cement so as to bond a temporary prosthetic to a person's teeth, or it may be used to simply fill a void within a person's teeth. However, at least one of the acid or the reaction between the acid and base components is believed to be responsible for causing tooth sensitivity or irritation.

In order to ameliorate or at least partially reduce the pain caused by the reaction of the acid and base components, the temporary dental cements according to the invention include one or more soothing agents that are able to greatly reduce or eliminate tooth sensitivity. The soothing agent typically comprises a hydrophobic oil. However, because the soothing oils typically constitute a relatively small fraction of the overall composition, they do not hinder the ability of the metal carboxylate polymer to form a good seal against a tooth surface. The relatively low concentration of the hydrophobic soothing oil yields a temporary bonding cement that is still sufficiently hydrophilic that it can be easily removed from the tooth without leaving behind an oily film, as typically occurs using conventional hydrophobic temporary bonding cements.

Examples of soothing agents that may be used within the scope of the invention include 2-ethoxybenzoic acid, 2-methoxy-4-methylphenol, eugenol, rosin, pine gum, tall oil, and the like.

The compositions according to the invention may also include a sugar or sugar-derivative (e.g., sorbitol) in order to form a temporary dental cement that can be more easily removed when needed preparatory to applying a permanent bonding cement to the person's tooth. The sugar or sugar-derivative may also help emulsify and/or suspend non-water soluble components within aqueous components or compositions prior to mixing them together.

Thickening agents, such as precipitated silicon dioxide, fumed silica, fumed aluminum oxide, colloidal silica, and the like may be used to increase the viscosity of the bonding compositions and form a composition having a desired consistency. The thickening agents may also impart thixotropy to the compositions in some cases to yield a composition that can be easily expressed or manipulated into a crack or crevice of a patient's tooth but which will not easily run off but remain in place while curing.

The temporary dental cements according to the invention typically comprise a multi-part composition in which the acid component is contained in one part and the base component is contained in another part. The parts may be solutions, suspensions, colloids, or a mixture of dry ingredients as desired. One or more soothing agents, the thickening agent, and other desired components may be contained in one or both of the acid and base parts. One or both of the acid and base components may include water, although it is certainly within the scope of the invention to provide one or both of the acid and base components as dry mixtures that are later mixed with water when it is desired to form the temporary dental cement. For example, water can be provided separately from the acid and base components if desired.

The temporary dental cements according to the invention may be included within a kit that also contains one or more additional components that facilitate the temporary repair process. For example, the kits may include a stirring device such as a metal, wooden or plastic rod, spatula, spoon and the like or other mixing devices known in the art. The kits may also include an application device, such as a spatula or a specially adapted syringe (e.g., multi-barrel syringe) and syringe tip suitable for placing the temporary dental cement onto a tooth in the desired location. The initially unmixed components can be preloaded into syringes, squeeze tubes or other appropriate dispensing devices. The kits may also include other compositions, such as an anesthetic composition that can be applied to a painful tooth to provide temporary anesthesia, a drying agent, a priming agent, and the like.

When it is desired to temporarily repair a broken or dislodged dental filling, prosthesis or appliance (hereinafter collectively referred to as "dental prosthesis"), the dental prosthesis may be removed or adjusted so as to allow the application of the temporary dental cement onto the tooth, followed by placement of the dental prosthesis. It is also within the scope of the invention to use the temporary dental cement to simply fill or seal a crack, crevice or other defect within a person's tooth to reduce pain until professional dental treatment can be obtained.

Because the temporary bonding cements according to the invention are hydrophilic, they can be easily removed preparatory to applying a permanent bonding agent or dental cement to the person's tooth. The temporary dental cements according to the present invention may be cleaned off as needed using water-based scouring agents, such as CON-SEPSIS SCRUB, which is available from Ultradent Products, Inc., located in South Jordan, Utah.

These and other features and advantages of the present invention will become more fully apparent from the following description and appended claims, or may be learned by the practice of the invention as set forth hereinafter.

DETAILED DESCRIPTION OF THE PREFERRED EMBODIMENTS

I. Introduction

The temporary dental cements according to the invention involve a reaction between an acidic polymer component and a base component in order to yield a temporary dental cement that is sufficiently hydrophilic that it can form a good seal against a person's tooth. They also include one or more soothing agents in order to reduce or eliminate the pain associated with at least one of the acid or the reaction between the acid and the base.

The temporary dental cements according to the invention can be used by dental practitioners to temporarily bond a prosthesis, dental appliance or other structure to the patient's tooth. It is also within the scope of the invention to provide temporary dental cements that are suitable for over-the-counter sale to persons who need to temporarily repair a broken or dislodged dental prosthesis or appliance or other defect without the assistance of a dental practitioner. The inventive dental cements can also be used as a temporary filling material to fill cracks, cavities or other defects until professional dental help can be obtained. Because the temporary dental cements according to the invention have greatly reduced pain or sensitivity compared to dental cements that rely on an acid-based reaction but do not include soothing agents, they can be used to temporarily repair a tooth that has not been anesthetized.

The temporary dental cements according to the invention are typically formed by mixing together initially separate parts that contain the reactive acid and base components together with one or more soothing agents, as well as optional components that may be included in order to yield compositions having desired properties. The temporary dental cements according to the invention may be sold separately or together as part of a dental repair kit, as will be discussed more fully below.

The term "about" when used in combination with a numeric value shall mean±10% of the numeric value. Thus, the effect of the term "about" is to define a range that is ±10% of the given numeric value.

A "reaction product" or "mixture product" is the product or products which result(s) when elements of a composition are mixed together.

II. Temporary Dental Cements

The temporary dental cements according to the invention include reactive components that are mixed just prior to application of the temporary dental cement to the person's tooth, together with one or more soothing agents that reduce the pain or sensitivity associated with one or both of the reactive components. The temporary dental cements may also include or one more sugars or sugar-derivatives, thickening agents, water and other components as desired to yield individual components having desired properties prior to mixing, as well as mixed dental cements having desired properties, both before and after the reactive components react together to cure the dental cement.

The term "temporary dental cement" should be broadly construed to encompass virtually any composition that can be formed by mixing together the components as set forth herein. There is no temporal limitation as to how long the "temporary dental cement" must be attached to a person's tooth (e.g., the "temporary dental cements" according to the invention may be attached to a tooth for days, weeks, months or even years as desired). In some cases the "temporary dental cement" may be used as a filling agent in order to temporarily repair a crack, cavity or other defect in a person's tooth until professional dental attention can be obtained. Thus, it is not necessary for a "temporary dental cement" to actually adhere a prosthesis, appliance or filling to the person's tooth.

A. Reactive Components

The reactive components include an acid and a base. Water may also be termed a "reactive component" when used to facilitate the acid-base reaction. The acid and base components are typically maintained in separate unmixed parts until it is desired to form a temporary dental cement according to the invention. At this time the initially separate parts are mixed together to form a temporary dental cement that undergoes a curing reaction within a predetermined period of time. This gives the user a window of time in which to apply the dental cement before complete curing or hardening occurs.

In one embodiment according to the invention, a first unmixed part comprises at least one polycarboxylic acid and a second unmixed part comprises at least one ion leaching agent or component. Water may also be included in one or both of the unmixed parts as desired. When mixed together, the polycarboxylic acid of the first part and the ion leaching agent of the second part form a hydrophilic matrix which can bond and seal against one or more dental substrates, such as a tooth, a dental appliance, a dental prosthesis or a dental filling. The initially separate parts may include other ingredients as described more filly below in order to yield unmixed and final mixed compositions having desired properties.

In the mixed composition, the polycarboxylic acid and the ion leaching agents contributed by the initially unmixed components are included in appropriate stoichiometric quantities in order to form a hardenable adhesive composition that reacts and cures in a desired time frame. Water will typically be present in the mixed composition in an amount sufficient to form a hardenable temporary dental cement having desired rheological properties. The water may also assist in the acid-based reaction between the polycarboxylic acid in the ion leaching agent.

Examples of polycarboxylic acids useful in the present invention include polyacrylic acid and polymethacrylic acid (e.g., having a molecular weight of 1,000 to 400,000).

The concentration of the polycarboxylic acid may be expressed both in terms of its concentration within the initially unmixed acid composition or part and in terms of its net concentration within the unmixed components used to form the mixed temporary dental cement.

The polycarboxylic acid will preferably be included in an amount in a range of about 10% to about 90% by weight of the initially unmixed acid component, more preferably in a range from about 20% to about 80% by weight, and most preferably in a range from about 30% to about 70% by weight of the initially unmixed acid component.

In terms of the overall temporary dental cement (i.e., the unmixed components used to form the dental cement), the polycarboxylic acid will preferably have a concentration in a range from about 5% to about 50% by weight of the overall temporary dental cement, more preferably in a range from about 10% to about 40% by weight, and most preferably in a range from about 15% to about 35% by weight of the overall temporary dental cement.

Examples of ion leaching agents suitable for use in forming temporary dental cements according to the invention include various metal oxides such as zinc oxide, magnesium oxide, calcium oxide, barium oxide, and aluminum oxide, and glass ionomers, such as barium aluminosilicate glass, strontium aluminosilicate glass, and other aluminosilicate glasses.

The concentration of the ion leaching agent may be expressed both in terms of its concentration within the initially unmixed base composition or part and also in terms of its net concentration within the unmixed components to form the temporary dental cement according to the invention.

The ion leaching agent will preferably have a concentration in a range of about 5% to about 90% by weight of the initially unmixed base component, more preferably in a range from about 10% to about 70% by weight, and most preferably in a range of about 20% to about 60% by weight of the initially unmixed base component.

With respect to the overall temporary dental cement (i.e., the unmixed components used to form the dental cement), the ion leaching agent will preferably have a concentration in a range from about 2% to about 50% by weight of the overall temporary dental cement, more preferably in a range from about 5% to about 35% by weight, and most preferably in a range of about 10% to about 30% by weight of the overall temporary dental cement.

In order for the acid and base components to react, the mixed temporary dental cements according to the invention typically include water in order to facilitate the acid-base reaction between the polycarboxylic acid and the ion leaching agent. The water may be included within one or both of the acid and base components, or it may be added as a completely separate component at the time the temporary dental cement is formed.

In general, the water will preferably have a net concentration relative to the overall temporary dental cement in a range of about 1% to about 50% by weight of the overall temporary dental cement, more preferably in a range from about 5% to about 40% by weight, and most preferably in a range from about 10% to about 30% by weight of the overall temporary dental cement.

If water is included within the acid component, it is typically included in an amount in a range of about 1% to about 99% by weight of the acid component, preferably in a range of about 5% to about 95% by weight, more preferably in a range of about 15% to about 85 by weight, and most preferably in a range of about 25% to about 75% by weight of the acid component.

If water is included within the base component, it is preferably included in a range of about 1% to about 90% by weight of the base component, more preferably in a range of about 5% to about 80% by weight, and most preferably in a range of about 10% to about 70% by weight of the base component.

B. Soothing Agents

The temporary dental cements according to the invention, in addition to the aforementioned reactive components, also include one or more soothing agents that serve to reduce or eliminate the pain or sensitivity associated with applying a mixture of the reactive components onto a freshly cut, exposed, damaged or otherwise sensitive tooth that is prone to pain or sensitivity. The soothing agents according to the invention are typically one or more hydrophobic oils that, when included within the temporary dental cements according to the invention, are able to offset the pain and sensitivity caused by one or more of the reactive components without preventing the temporary dental cements from forming a good seal against a dental substrate.

Examples of soothing agents within the scope of the invention include 2-ethoxybenzoic acid, 2-methoxy-4-methylphenol, eugenol, rosin, pine gum, tall oil, and the like. Another constituent that may optionally be used to provide a desensitizing effect is potassium nitrate ($KNO_3$).

The soothing agents may be included within one or both of the unmixed components used to form the temporary dental cements according to the invention. In one embodiment, a soothing agent system comprising one or both of 2-ethoxybenzoic acid and 2-methoxy-4-methylphenol is included within the acid component since they are more compatible with the polyacrylic acid (being acidic themselves). Nevertheless, it is certainly within the scope of the invention to select soothing agents that are compatible with the ion leaching agent.

When included within the acid component, the soothing agents are preferably included in an amount in a range of about 0.1% to about 50% by weight of the acid component, more preferably in a range of about 2% to about 40% by weight, and most preferably in a range of about 6% to about 30% by weight of the acid component.

The soothing agents are preferably included in an amount in a range of about 0.05% to about 25% by weight of the overall temporary dental cement, more preferably in a range of about 1% to about 20% by weight, and most preferably in a range of about 3% to about 15% by weight of the overall temporary dental cement.

C. Sugar and Sugar Derivatives

One or more sugars or sugar-derivatives may be added to one or both of the acid and base components as desired in order to yield compositions having desired properties. For example, the sugar can act as a colloidal suspending agent to form a stable colloidal suspension for the ion leaching agent and water. This helps to prevent the ion leaching agent for settling out of the suspension. The sugar or sugar-derivative may also alter the final strength properties of temporary dental cement, typically in a manner that weakens the cement so that it is more easily removed when desired.

When included within the temporary dental cements according to the invention, the sugar or sugar-derivative is preferably included in an amount in a range of about 0.5% to about 35% by weight of the temporary dental cement, more preferably in a range of about 2.5% to about 30% by weight, and most preferably in a range of about 7.5% to about 20% by weight of the temporary dental cement.

A variety of different sugars or sugar-derivatives may be employed within the temporary dental cements according to the invention. Examples of six-carbon sugars which are useful in the present invention as colloidal suspending agents and which allow the combined components to form a temporary dental cement include sorbitol, galactol, mannitol, mixtures thereof, and derivatives thereof. In one embodiment, sorbitol may be employed independently from other sugars. In another embodiment, a combination of sorbitol and mannitol, a combination or sorbitol and galactol, or a combination of galactol and mannitol may be employed in the temporary cement composition. Galactol or mannitol may also be employed independently from each other and/or other six-carbon sugars.

A preferred chemical formula for a six carbon sugar of the present invention is $C_6H_{14}O_6$. A preferred chemical formula for a five-carbon sugar employed in the invented temporary dental cement composition is $C_5H_{12}O_5$. An example of a useful five-carbon sugar is xylitol, which also can impart an anticariogenic and antimicrobial effect in the present invention, as well as acting as a colloidal suspending agent, a matrix weakener and having the other benefits of sugars generally.

D. Thickening Agents

It is within the scope of the invention to include one or more thickening agents within one or both of the acid and base components in order to yield a composition having a desired level of viscosity and/or thixotropy. An example of a useful thickening agent is fumed silica. Other thickening agents according to the invention include a wide variety of other particulate inorganic fillers such as precipitated silica, colloidal silica, fumed aluminum oxide, titanium dioxide, silicon carbon and the like.

In addition to particulate thickening agents, it is within the scope of the invention to include one or more polymeric thickening agents.

When a thickening agent is included within the temporary dental cements according to the invention, the thickening agent will preferably have a concentration in a range of about 1% to about 40% by weight of the overall temporary dental cement, more preferably in a range of about 5% to about 35% by weight, and most preferably in a range of about 10% to about 30% by weight of the overall temporary dental cement.

E. Other Components

It is within the scope of the invention to include other additives or adjuvents as desired to yield compositions having desired properties. These include polyols, solvents, sweeteners, antimicrobial agents, anticariogenic agents, and the like.

Examples of polyols that may be included within the temporary dental cements according to the invention include glycerin, propylene glycol, polyethylene glycol, polypropylene glycol and the like. Specific examples include polyethylene glycol having a molecular weight in a range of about 300 to 8,000 and polypropylene glycol having a molecular weight in a range of about 300 to 8,000.

Examples of solvents that can be used within temporary dental cements according to the invention include ethanol, isopropyl alcohol, acetone, and the like.

Examples of antimicrobial agents include chlorhexidine, 1,1'-hexamethylene bis(5(p-chlorophenyl)biguanide), cetyl pyridinium chloride, benzalkonium chloride, cetyl pyridinium bromide, methyl 4-hydroxybenzoate and propylparaben (propyl p-hydroxybenzoate).

Examples of anticariogenic agents include any of the known fluoride salts that are used in the dental arts to strengthen dental enamel.

III. Kits for Temporary Restoration

As will be appreciated from the discussion above, kits according to the invention for temporarily restoring a tooth will generally comprise initially separate acid and base compositions. Kits according to the invention may also contain one or more additional components that facilitate the temporary repair process. For example, kits according to the invention may include a stirring device such as a metal, wooden, or plastic rod, spatula, spoon and the like. The kits may include an application device, such as a spatula or a specially adapted syringe and syringe tip suitable for placing the temporary dental cement within a desired location on a tooth.

Kits according to the invention may include other compositions that assist or augment the temporary dental cements, such as an anesthetic composition, a drying agent, a priming agent, and the like.

Initially unmixed parts or components can be preloaded into syringes, squeeze tubes or other appropriate dispensing devices, or they may be packaged within jars or other storage devices not suitable for dispensing and then drawn into a syringe or other dispensing device. Initially unmixed acid and base components may be mixed together in any ratio. In the case of over-the-counter products, it may be advantageous to formulate the acid and base components so that they can be mixed in a 1:1 ratio for simplicity. Dispensing devices can be selected to help mix the initially separate components in a desired ratio.

IV. Method of Using Inventive Temporary Dental Cements

The temporary dental cements according to the invention may be used in the same manner as other temporary dental cements known in the art, including both hydrophilic and hydrophobic temporary dental cements. They may be used by a dental practitioner in order to temporarily bond a temporary crown, dental appliance or other prosthesis to a person's tooth during a dental procedure. They may be used as a temporary filling material that can easily be removed at a later time.

In the case of over-the-counter temporary dental cements according to the invention, they may be used by a non-dental practitioner to repair a damaged tooth, crown, dental appliance or other dental prosthetic prior to or instead of visiting a dental practitioner. They can be used to temporarily fill a cavity as a temporary filling material prior to visiting a dental practitioner.

The temporary dental cements may be used alone or in combination with other auxiliary or complementary compositions. For example, an anesthetic composition may be applied to the tooth to temporarily eliminate pain prior to applying the temporary dental cement. An antiseptic or antimicrobial composition may be used to eliminate or at least inhibit infection prior to applying the temporary dental cement. Other compositions such as drying agents, priming agents, and the like may also be applied as desired prior to application of the temporary dental cement.

When it is desired to remove the temporary dental cement it can be cleaned off as needed using water or water-based detergents or scrubbing agents, an example of which is CONSEPSIS SCRUB, available from Ultradent Products, Inc. Following the removal of the temporary dental cement, the tooth may be prepared using restorative compositions known in the art. Because the inventive compositions do not contain high concentrations of hydrophobic oils that can remain adhered to the dental substrate, the temporary dental cements according to the invention leave a relatively clean surface to which a restorative composition may subsequently be applied.

V. Examples of the Invention

The following examples set forth various exemplary hemostatic compositions and dental etching compositions according to the invention. These examples are intended to be purely exemplary and should not be viewed as limiting the scope of the present invention. Examples that were actually made are set forth in past tense, while hypothetical examples are set forth in present tense.

The temporary dental cements according to the invention typically comprise initially separate and unmixed base and acid components. Therefore, the following examples are more particularly directed to individual base and acid components. It should be understood that any of the base components may be mixed with any of the acid components to form a mixed temporary dental cement (e.g., in a 1:1 ratio).

BASE EXAMPLE 1

A base composition was formed by mixing together the following components in the stated amounts:

| Ingredient | Concentration by Weight |
| --- | --- |
| Distilled Water | 52.8% |
| Zinc Oxide | 45% |
| Fumed silica (Aerosil 200) | 2% |
| Polyethylene glycol (600 MW) | 0.2% |

BASE EXAMPLE 2

A base composition was formed by mixing together the following components in the stated amounts:

| Ingredient | Concentration by Weight |
| --- | --- |
| Distilled $H_2O$ | 50.5% |
| Zinc Oxide | 45% |
| Aerosil 200 | 4% |
| PEG 600 | 0.5% |

BASE EXAMPLE 3

A base composition was formed by mixing together the following components in the stated amounts:

| Ingredient | Concentration by Weight |
| --- | --- |
| Distilled $H_2O$ | 60.5% |
| Zinc Oxide | 35% |
| Aerosil 200 | 4% |
| PEG 600 | 0.5% |

BASE EXAMPLE 4

A base composition was formed by mixing together the following components in the stated amounts:

| Ingredient | Concentration by Weight |
| --- | --- |
| Distilled $H_2O$ | 36.6% |
| Zinc Oxide | 60% |
| Fumed silica (Cabosil M-5) | 3% |
| PEG 600 | 0.4% |

BASE EXAMPLE 5

A base composition was formed by mixing together the following components in the stated amounts:

| Ingredient | Concentration by Weight |
| --- | --- |
| Distilled $H_2O$ | 27.6% |
| Cabosil M-5 | 2% |
| PEG 300 | 0.4% |
| Glycerin | 30% |
| Zinc Oxide | 40% |

BASE EXAMPLE 6

A base composition was formed by mixing together the following components in the stated amounts:

| Ingredient | Concentration by Weight |
| --- | --- |
| PEG 600 | 26% |
| Glycerin | 30% |
| Cabosil M-5 | 4% |
| Zinc Oxide | 40% |

BASE EXAMPLE 7

A base composition was formed by mixing together the following components in the stated amounts:

| Ingredient | Concentration by Weight |
| --- | --- |
| Xylitol | 25% |
| Distilled Water | 35.6% |
| Aerosil 200 | 2% |
| PEG 600 | 0.4% |
| Zinc Oxide | 35% |
| Ethanol | 2% |

BASE EXAMPLE 8

A base composition was formed by mixing together the following components in the stated amounts:

| Ingredient | Concentration by Weight |
| --- | --- |
| Sorbitol (70% in water) | 43% |
| Sorbitol Powder | 7% |
| Precipitated $SiO_2$ (Zeo 113) | 13.2% |
| Zinc Oxide | 35% |
| Ethanol | 1.8% |

BASE EXAMPLE 9

A base composition was formed by mixing together the following components in the stated amounts:

| Ingredient | Concentration by Weight |
| --- | --- |
| Xylitol | 25% |
| Water | 25.6% |
| Aerosil | 2% |
| PEG 600 | 0.4% |
| Zinc Oxide | 45% |
| Ethanol | 2 % |

BASE EXAMPLE 10

A base composition was formed by mixing together the following components in the stated amounts:

| Ingredient | Concentration by Weight |
| --- | --- |
| Distilled $H_2O$ | 33.3% |
| PEG 20,000 | 11.7% |
| Zeo 113 | 13.3% |
| Zinc Oxide | 41.67% |

BASE EXAMPLE 11

A base composition was formed by mixing together the following components in the stated amounts:

| Ingredient | Concentration by Weight |
| --- | --- |
| Distilled $H_2O$ | 33.3% |
| PEG 20,000 | 11.7% |
| Zeo113 | 13.3% |
| Zinc Oxide | 41.67% |

BASE EXAMPLE 12

A base composition was formed by mixing together the following components in the stated amounts:

| Ingredient | Concentration by Weight |
|---|---|
| Distilled $H_2O$ | 10.2% |
| Sorbitol Powder | 27.3% |
| Ethanol | 17.1% |
| Zinc Oxide | 43% |
| Aerosil 200 | 2% |
| PEG 600 | 0.4% |

BASE EXAMPLE 13

A base composition was formed by mixing together the following components in the stated amounts:

| Ingredient | Concentration by Weight |
|---|---|
| 2-Ethoxybenzoic Acid | 58% |
| Zinc Oxide | 40% |
| Aerosil 200 | 2% |

This base composition did not exhibit good long-term stability because the 2-ethoxybenzoic acid evidently reacted with the zinc oxide in an acid-based reaction.

BASE EXAMPLE 14

A base composition was formed by mixing together the following components in the stated amounts:

| Ingredient | Concentration by Weight |
|---|---|
| Ethanol | 51% |
| Zinc Oxide | 45% |
| Aerosil 200 | 4% |

BASE EXAMPLE 15

A base composition was formed by mixing together the following components in the stated amounts:

| Ingredient | Concentration by Weight |
|---|---|
| 2-Methoxy-4-methylphenol | 54% |
| Zinc Oxide | 42% |
| Aerosil 200 | 4% |

This base composition was more stable than the composition of Example 13 in that the 2-methoxy-4-methylphenol did not appear to appreciably react with the zinc oxide.

BASE EXAMPLE 16

A base composition was formed by mixing together the following components in the stated amounts:

| Ingredient | Concentration by Weight |
|---|---|
| Sorbitol (70% in water) | 44.8% |
| Precipitated $SiO_2$ | 20% |
| Zinc Oxide | 42% |
| Pigments | 0.2% |

The pigments were added to give the base composition of Example 16 a slightly contrasting color compared to the acid composition. This helps the user determine the extent of mixing of the two components.

ACID EXAMPLE 1

An acid composition was formed by mixing together the following components in the stated amounts:

| Ingredient | Concentration by Weight |
|---|---|
| Distilled Water | 25.7% |
| Polyacrylic Acid (60% in water) | 55.8% |
| Aerosil 200 | 6% |
| Zeo 113 | 12% |
| PEG 600 | 0.5% |

Because the acid composition of this example did not include any of the preferred soothing agents as disclosed, temporary dental cements according to the invention can be made by mixing this acid composition with a base composition that contains one or more soothing agents (e.g., Base Examples 13 and 15).

ACID EXAMPLE 2

An acid composition was formed by mixing together the following components in the stated amounts:

| Ingredient | Concentration by Weight |
|---|---|
| Polyacrylic Acid (25% in water) (M.W. 240,000) | 93% |
| Aerosil 200 | 7% |

Because the acid composition of this example did not include any of the preferred soothing agents as disclosed, temporary dental cements according to the invention can be made by mixing this acid composition with a base composition that contains one or more soothing agents (e.g., Base Examples 13 and 15).

ACID EXAMPLE 3

An acid composition was formed by mixing together the following components in the stated amounts:

| Ingredient | Concentration by Weight |
|---|---|
| Polyacrylic Acid (25% in water) (M.W. 240,000) | 50% |

-continued

| Ingredient | Concentration by Weight |
|---|---|
| Polyacrylic Acid (50% in water) M.W. 5,000 | 42% |
| Aerosil 200 | 8% |

Because the acid composition of this example did not include any of the preferred soothing agents as disclosed, temporary dental cements according to the invention can be made by mixing this acid composition with a base composition that contains one or more soothing agents (e.g., Base Examples 13 and 15).

ACID EXAMPLE 4

An acid composition was formed by mixing together the following components in the stated amounts:

| Ingredient | Concentration by Weight |
|---|---|
| Polyacrylic Acid (25% in water) (M.W. 240,000) | 50% |
| 2-Methoxybenzoic Acid | 42% |
| Aerosil 200 | 8% |

Because the acid composition of this example included a soothing agent (2-methoxybenzoic acid), temporary dental cements according to the invention can be made by mixing this acid composition with any base composition that contains an appropriate ion leaching agent that can react with the polyacrylic acid in an acid-base reaction (e.g., Base Examples 1–16).

ACID EXAMPLE 5

An acid composition was formed by mixing together the following components in the stated amounts:

| Ingredient | Concentration by Weight |
|---|---|
| Polyacrylic Acid (25% in water) (M.W. 240,000) | 83% |
| 2-Methoxybenzoic acid | 10% |
| Aerosil 200 | 7% |

Because the acid composition of this example included a soothing agent (2-methoxybenzoic acid), temporary dental cements according to the invention can be made by mixing this acid composition with any base composition that contains an appropriate ion leaching agent that can react with the polyacrylic acid in an acid-base reaction (e.g., Base Examples 1–16).

ACID EXAMPLE 6

An acid composition was formed by mixing together the following components in the stated amounts:

| Ingredient | Concentration by Weight |
|---|---|
| Polyacrylic Acid (25% in water) (M.W. 240,000) | 82.5% |

-continued

| Ingredient | Concentration by Weight |
|---|---|
| 2-Methoxybenzoic acid | 10% |
| Aerosil 200 | 7% |
| Acetic Acid | 0.5% |

Because the acid composition of this example included a soothing agent (2-methoxybenzoic acid), temporary dental cements according to the invention can be made by mixing this acid composition with any base composition that contains an appropriate ion leaching agent that can react with the polyacrylic acid in an acid-base reaction (e.g., Base Examples 1–16).

ACID EXAMPLE 7

An acid composition was formed by mixing together the following components in the stated amounts:

| Ingredient | Concentration by Weight |
|---|---|
| Polyacrylic Acid (25% in water) (M.W. 240,000) | 82% |
| 2-Methoxybenzoic acid | 10% |
| Aerosil 200 | 7% |
| 2-Methoxy-4-methylphenol | 1% |

Because the acid composition of this example included soothing agents (2-methoxybenzoic acid and 2-methoxy-4-methylphenol), temporary dental cements according to the invention can be made by mixing this acid composition with any base composition that contains an appropriate ion leaching agent that can react with the polyacrylic acid in an acid-base reaction (e.g., Base Examples 1–16).

ACID EXAMPLE 8

An acid composition was formed by mixing together the following components in the stated amounts:

| Ingredient | Concentration by Weight |
|---|---|
| Polyacrylic Acid (25% in water) (M.W. 240,000) | 32.5% |
| Polyacrylic Acid (50% in water) (M.W. 5,000) | 50% |
| 2-Methoxybenzoic acid | 10% |
| Aerosil 200 | 7% |
| 2-Methoxy-4-methylphenol | 0.5% |

Because the acid composition of this example included soothing agents (2-methoxybenzoic acid and 2-methoxy-4-methylphenol), temporary dental cements according to the invention can be made by mixing this acid composition with any base composition that contains an appropriate ion leaching agent that can react with the polyacrylic acid components in an acid-base reaction (e.g., Base Examples 1–16).

ACID EXAMPLE 9

An acid composition was formed by mixing together the following components in the stated amounts:

| Ingredient | Concentration by Weight |
| --- | --- |
| Polyacrylic Acid (60% in water) (M.W. 2100) | 77% |
| 2-Methoxybenzoic acid | 15% |
| 2-Methoxy-4-methylphenol | 1% |
| Aerosil | 7% |

Because the acid composition of this example included soothing agents (2-benzoic methoxybenzoic acid and 2-methoxy-4-methylphenol), temporary dental cements according to the invention can be made by mixing this acid composition with any base composition that contains an appropriate ion leaching agent that can react with the polyacrylic acid in an acid-base reaction (e.g., Base Examples 1–16).

The present invention may be embodied in other specific forms without departing from its spirit or essential characteristics. The described embodiments are to be considered in all respects only as illustrated and not restrictive. The scope of the invention is, therefore, indicated by the appended claims rather than by the foregoing description. All changes which come within the meaning and range of equivalency of the claims are to be embraced within their scope.

What is claimed is:

1. A multipart composition comprising at least two initially separate parts which, upon mixing the parts together, form a mixed temporary dental cement that is initially deformable and suitable for placement onto a person's tooth and which hardens over time, the multipart composition comprising:
   at least one polycarboxylic acid contained in at least one of the initially separate parts;
   at least one ion leaching component contained in at least one other of the initially separate parts that does not contain the polycarboxylic acid;
   at least one soothing agent contained in at least one of the initially separate parts in an amount so as to reduce tooth sensitivity caused by the mixed temporary dental cement compared to tooth sensitivity that would be caused by the dental cement in the absence of the soothing agent,
      the soothing agent comprising at least one of 2-ethoxybenzoic acid, 2-methyl-4-methylphenol, eugenol, tall oil, rosin, or pine gum; and
   optionally water contained in at least one of the initially separate parts.

2. A multi-part composition as defined in claim 1, the polycarboxylic acid comprising polyacrylic acid.

3. A multi-part composition as defined in claim 1, the polycarboxylic acid having a concentration of about 5% to about 50% by weight of the mixed temporary dental cement.

4. A multi-part composition as defined in claim 1, the polycarboxylic acid having a concentration of about 10% to about 40% by weight of the mixed temporary dental cement.

5. A multi-part composition as defined in claim 1, the polycarboxylic acid having a concentration of about 15% to about 35% by weight of the mixed temporary dental cement.

6. A multi-part composition as defined in claim 1, the ion leaching agent comprising at least one of a metal oxide or an aluminosilicate glass.

7. A multi-pan composition as defined in claim 6, the ion leaching agent comprising zinc oxide.

8. A multi-part composition as defined in claim 6, the ion leaching agent comprising at least one of an alkaline earth metal oxide, a transition metal oxide, or an alkaline earth metal aluminosilicate glass.

9. A multi-pan composition as defined in claim 1, the ion leaching agent having a concentration of about 2% to about 50% by weight of the mixed temporary dental cement.

10. A multi-pan composition as defined in claim 1, the ion leaching agent having a concentration of about 5% to about 35% by weight of the mixed temporary dental cement.

11. A multi-part composition as defined in claim 1, the ion leaching agent having a concentration of about 10% to about 30% by weight of the mixed temporary dental cement.

12. A multi-part composition as defined in claim 1, the soothing agent comprising at least one of 2-ethoxybenzoic acid or 2-methyl-4-methylphenol.

13. A multi-part composition as defined in claim 1, further comprising potassium nitrate within at least one of the initially separate parts to provide a desensitizing effect in addition to the soothing agent.

14. A multi-part composition as defined in claim 1, the soothing agent having a concentration of about 0.05% to about 25% by weight of the mixed temporary dental cement.

15. A multi-part composition as defined in claim 1, the soothing agent having a concentration of about 1% to about 20% by weight of the mixed temporary dental cement.

16. A multi-part composition as defined in claim 1, the soothing agent having a concentration of about 3% to about 15% by weight of the mixed temporary dental cement.

17. A multi-part composition as defined in claim 1, further comprising at least one sugar or sugar derivative contained in at least one of the initially separate parts.

18. A multi-part composition as defined in claim 17, the sugar or sugar derivative comprising at least one of five-carbon or six-carbon sugars or derivatives.

19. A multi-part composition as defined in claim 17, the sugar or sugar derivative having a chemical formula of $C_6H_{14}O_6$.

20. A multi-part composition as defined in claim 17, the sugar or sugar derivative comprising sorbitol.

21. A multi-part composition as defined in claim 17, the sugar or sugar derivative comprising at least one of mannitol or galactol.

22. A multi-part composition as defined in claim 17, the sugar or sugar derivative having a concentration of about 0.5% to about 35% by weight of the mixed temporary dental cement.

23. A multi-part composition as defined in claim 1, further comprising at least one thickening agent contained in at least one of the initially separate parts.

24. A multi-part composition as defined in claim 23, the thickening agent comprising at least one of fumed silica, fumed aluminum oxide, colloidal silica, or precipitated silica.

25. A multi-part composition as defined in claim 23, the thickening agent having a concentration of about 1% to about 40% by weight of the mixed temporary dental cement.

26. A multi-part composition as defined in claim 1, the multi-part composition comprising water having a concentration of about 5% to about 35% by weight of the mixed temporary dental cement.

27. A multi-part composition as defined in claim 1, the multi-part composition comprising water having a concentration of about 10% to about 30% by weight of the mixed temporary dental cement.

28. A dental repair system comprising a syringe and the multi-part composition of claim 1, each initially separate part of the multi-part composition being contained in a corresponding syringe barrel of the syringe.

29. A dental repair system comprising a multi-barrel syringe and the multi-part composition of claim 1, the initially separate part containing the polycarboxylic acid being contained in a first barrel of the multi-barrel syringe and the initially separate part containing the ion leaching agent being contained in a second barrel of the multi-barrel syringe.

30. A multi-part composition as defined in claim 1, at least one of the initially separate parts having a color that differs from at least one other of the initially separate parts.

31. A bonding system for temporarily bonding a dental prosthetic to a person's tooth, comprising:

a first composition comprising at least one polycarboxylic acid, at least one soothing agent, and water,
the soothing agent comprising at least one of 2-ethoxybenzoic acid, 2-methyl-4-methylphenol, eugenol, tall oil, rosin, or pine gum; and a second composition comprising at least one ion leaching agent, at least one of a sugar or sugar derivative, and water, the first and second compositions, upon being mixed together, forming a temporary dental cement that is initially deformable and suitable for placement onto a person's tooth and which hardens over time in order to temporarily bond a dental prosthetic to a tooth, the soothing agent being included in an amount so as to reduce tooth sensitivity caused by the temporary dental cement compared to tooth sensitivity that would be caused by the dental cement in the absence of the soothing agent.

32. A kit for use in temporarily repairing a person's tooth comprising:

(a) at least one temporary dental prosthetic; and (b) at least one multi-part composition comprising at least two initially separate parts which, upon mixing the parts together, form a mixed temporary dental cement that is initially deformable and suitable for placement onto a person's tooth and which hardens over time, the multipart composition comprising:

at least one polycarboxylic acid contained in at least one of the initially separate parts;

at least one ion leaching component contained in at least one other of the initially separate parts that does not contain the polycarboxylic acid;

at least one soothing agent contained in at least one of the initially separate parts in an amount so as to reduce tooth sensitivity caused by the mixed temporary dental cement compared to tooth sensitivity that would be caused by the dental cement in the absence of the soothing agent,
the soothing agent comprising at least one of 2-ethoxybenzoic acid, 2-methyl-4-methylphenol, eugenol, tall oil, rosin, or pine gum; and optionally water contained in at least one of the initially separate parts.

33. A kit as defined in claim 32, further comprising at least one syringe into which at least one of the initially separate parts of the multi-part composition is loaded.

34. A kit as defined in claim 32, further comprising at least one mixing device that may be used to facilitate mixing of the initially separate parts.

35. A kit as defined in claim 32, further comprising at least one applicator that may be used to apply the mixed temporary dental cement onto a tooth.

36. A kit as defined in claim 32, further comprising a topical anesthetic composition suitable for treating at least one of dental or gingival pain.

37. A method for repairing a person's tooth comprising:

(a) mixing together a polycarboxylic acid, an ion leaching agent, a soothing agent, and water to form a temporary dental cement that is initially deformable and suitable for placement onto a person's tooth and which hardens over time, the soothing agent being included in an amount so as to reduce tooth sensitivity caused by the temporary dental cement compared to tooth sensitivity that would be caused by the dental cement in the absence of the soothing agents,
the soothing agent comprising at least one of 2-ethoxybenzoic acid, 2-methyl-4-methylphenol, eugenol, tall oil, rosin, or pine gum;

(b) placing at least a portion of the temporary dental cement composition onto a tooth surface; and (c) allowing the temporary dental cement to harden.

38. A method as defined in claim 37, further comprising placing a dental prosthesis over at least a portion of the temporary dental cement prior to hardening of the temporary dental cement, the temporary dental cement bonding the dental prosthesis to the person's tooth.

39. A method as defined in claim 37, further comprising removing the dental prosthesis.

40. A method as defined in claim 39, further comprising removing at least a portion of the temporary dental cement and applying a permanent bonding agent to the tooth.

41. A method as defined in claim 40, further comprising placing a permanent dental prosthesis over at least a portion of the permanent bonding agent.

42. A multipart composition comprising at least two initially separate parts which, upon mixing the parts together, form a mixed temporary dental cement that is initially deformable and suitable for placement onto a person's tooth and which hardens over time, the multipart composition comprising:

at least one polycarboxylic acid contained in at least one of the initially separate parts;

at least one ion leaching component contained in at least one other of the initially separate parts that does not contain the polycarboxylic acid;

at least one soothing agent contained in at least one of the initially separate parts in an amount so as to reduce tooth sensitivity caused by the mixed temporary dental cement compared to tooth sensitivity that would be caused by the dental cement in the absence of the soothing agent, the soothing agent comprising at least one organic compound; and optionally water contained in at least one of the initially separate parts.

43. A multipart composition as defined in claim 42, further comprising potassium nitrate to provide a desensitizing effect in a addition to the soothing agent.

* * * * *

UNITED STATES PATENT AND TRADEMARK OFFICE
CERTIFICATE OF CORRECTION

PATENT NO.      : 6,814,794 B2
DATED           : November 9, 2004
INVENTOR(S)     : Peter M. Allred It is certified that error appears in the above-identified patent and that said Letters Patent is hereby corrected as shown below:

Title page,
Item [56], References Cited U.S. PATENT DOCUMENTS, after
"5,554,027 A    9/1996" change "Br.ang.nemark" to -- Brånemark --

Column 3,
Line 59, after "patient's tooth" remove "but"
Line 60, change "run off but remain" to -- run off, but will remain --

Column 7,
Line 20, after "15% to about" change "85" to -- 85% --

Column 8,
Line 34, before "other six-carbon sugars." insert -- the --

Column 9,
Line 29, after "spoon and the like" insert -- or other mixing devices know in the art --
Line 31, after "specially adapted syringe" insert -- (e.g. multi-barrel syringe) --

Column 12,
Under "BASE EXAMPLE 10", replace the contents of the table with the following:

| Ingredient | Concentration by Weight |
|---|---|
| Sorbitol | 33% |
| Sorbital Powder | 7% |
| Zeo 113 | 13.2% |
| Zinc Oxide | 45% |
| Ethanol | 1.8% --|

Under "BASE EXAMPLE 11", table line 3, change "Zeo113" to -- Zeo 113 --

UNITED STATES PATENT AND TRADEMARK OFFICE
CERTIFICATE OF CORRECTION

PATENT NO. : 6,814,794 B2
DATED : November 9, 2004
INVENTOR(S) : Peter M. Allred It is certified that error appears in the above-identified patent and that said Letters Patent is hereby corrected as shown below:

Column 29,
Line 61, before "addition to the soothing agent." remove "a"

Signed and Sealed this

Fourteenth Day of June, 2005

JON W. DUDAS
*Director of the United States Patent and Trademark Office*

UNITED STATES PATENT AND TRADEMARK OFFICE
CERTIFICATE OF CORRECTION

PATENT NO. : 6,814,794 B2
APPLICATION NO. : 10/288775
DATED : November 9, 2004
INVENTOR(S) : Allred It is certified that error appears in the above-identified patent and that said Letters Patent is hereby corrected as shown below:

In the Claims

Claim 1, Column 17
Line 50, change "2-methyl-4-methyphenol" to -- 2-methoxy-4-methyphenol --

Claim 31, Column 19
Line 20, change "2-methyl-4-methyphenol" to -- 2-methoxy-4-methyphenol --
Line 57, change "2-methyl-4-methyphenol" to -- 2-methoxy-4-methyphenol --

Claim 37, Column 20
Line 20, change "2-methyl-4-methyphenol" to -- 2-methoxy-4-methyphenol --

Signed and Sealed this
Twelfth Day of November, 2013

Teresa Stanek Rea
*Deputy Director of the United States Patent and Trademark Office*